United States Patent [19]

Engel et al.

[11] 4,443,452

[45] Apr. 17, 1984

[54] DIBENZODIAZEPINONES, PHARMACEUTICAL COMPOSITIONS THEREOF AND METHOD OF USE THEREOF

[75] Inventors: Wolfhard Engel, Biberach; Günter Trummlitz, Warthausen; Günther Schmidt; Wolfgang Eberlein, both of Biberach, all of Fed. Rep. of Germany; Rudolf Hammer, Milan; Piero del Soldato, Monza, both of Italy

[73] Assignee: Dr. Karl Thomae GmbH, Biberach an der Riss, Fed. Rep. of Germany

[21] Appl. No.: 462,378

[22] Filed: Jan. 31, 1983

[30] Foreign Application Priority Data

Feb. 6, 1982 [DE] Fed. Rep. of Germany ....... 3204158

[51] Int. Cl.³ .................... A61K 31/55; C07D 403/12; C07D 403/14
[52] U.S. Cl. .................................. 424/256; 424/263; 424/267; 260/239.3 T
[58] Field of Search .................. 260/239.3 T; 424/267, 424/263, 256

[56] References Cited

U.S. PATENT DOCUMENTS 3,634,408  1/1972  Schmidt et al. .............. 260/238.3 T
3,749,785  7/1973  Schmidt et al. .............. 260/239.3 T
4,377,576  3/1983  Schmidt et al. .............. 260/239.3 T Primary Examiner—Robert T. Bond
Attorney, Agent, or Firm—Hammond & Littell, Weissenberger and Muserlian

[57] ABSTRACT

This invention relates to compounds of the formula

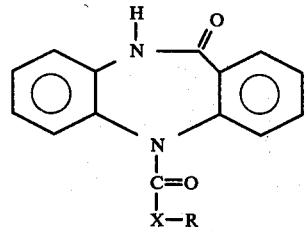

wherein

X is oxygen, —NH—, or —NCH₃— and

R is 1-methyl-4-piperidinyl, 4-methyl-1-piperazinyl, endo-8-methyl-8-azabicyclo[3.2.1]oct-3-yl, or exo-8-methyl-8-acabicyclo[3.2.1]oct-3-yl, each of which may optionally have an additional methyl substituent, a diastereomer or enantiomer thereof, or a non-toxic, pharmacologically acceptable acid addition salt thereof with an inorganic or organic acid.

4 Claims, No Drawings

DIBENZODIAZEPINONES, PHARMACEUTICAL COMPOSITIONS THEREOF AND METHOD OF USE THEREOF

FIELD OF THE INVENTION

This invention relates to novel substituted dibenzodiazepinones. More particularly, this invention relates to novel substituted dibenzodiazepinones and non-toxic acid addition salts thereof, methods of preparing these compounds, pharmaceutical compositions containing them as active ingredients, and a method of using them as anti-ulcerogenics and gastric acid secretion inhibitors.

BACKGROUND OF THE INVENTION

In German Offenlegungsschrift No. 1,795,176, certain dibenzodiazepinones having anti-ulcerogenic and scretion-inhibiting properties are described. U.S. Pat. No. 3,953,430 discloses substituted dibenzodiazepines having antidepressant and analgesic properties.

OBJECTS OF THE INVENTION

It is an object of the invention to provide novel substituted dibenzodiazepinones having useful pharmacodynamic properties superior to those of the related compounds disclosed in the prior art.

It is also an object of the invention to provide pharmaceutical compositions containing substituted dibenzodiazepinones as active ingredients.

It is a further object of the invention to provide a method of using substituted dibenzodiazepinones as antiulcerogenics and gastric acid secretion inhibitors.

These and other objects of the invention will become more apparent from the discussion below.

DETAILED DESCRIPTION OF THE INVENTION

The present invention relates to a novel class of substituted dibenzodiazepinones represented by the formula

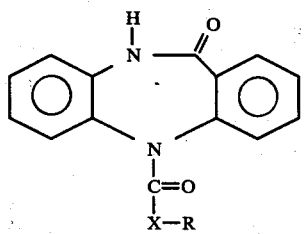

(I)

wherein

X is oxygen, —NH—, or —NCH$_3$— and

R is 1-methyl-4-piperidinyl, 4-methyl-1-piperazinyl, 3α-tropanyl, or 3β-tropanyl, each of which can optionally have another methyl substituent, and the non-toxic, pharmacologically acceptable acid addition salts thereof.

The compounds of Formula I may be obtained in the form of their pharmacologically acceptable salts after reaction with inorganic or organic acids. Suitable acids include, for example, hydrochloric, hydrobromic, sulfuric, methylsulfuric, phosphoric, tartaric, fumaric, citric, maleic, succinic, gluconic, malic, p-toluenesulfonic, methanesulfonic, and anidosulfonic acid.

The following compounds are illustrative of the invention:

(a) 5,10-dihydro-5-{[(1-methyl-4-piperidinyl)oxy]carbonyl}-11H-dibenzo[b,e][1,4]diazepin-11-one;

(b) cis-5,10-dihydro-5-{[(1,2-dimethyl-4-piperidinyl)oxy]-carbonyl}-11H-dibenzo[b,e][1,4]diazepin-11-one;

(c) trans-5,10-dihydro-5-{[(1,2-dimethyl-4-piperidinyl)oxy]-carbonyl}-11H-dibenzo[b,e][1,4]diazepin-11-one;

(d) cis-5,10-dihydro-5-{[(1,3-dimethyl-4-piperidinyl)oxy]-carbonyl)-11H-dibenzo[b,e][1,4]diazepin-11-one;

(e) trans-5,10-dihydro-5-{[(1,3-dimethyl-4-piperidinyl)oxy]-carbonyl}-11H-dibenzo[b,e][1,4]diazepin-11-one;

(f) 5,10-dihydro-5-{[(1-methyl-4-piperidinyl)amino]carbonyl}-11H-dibenzo[b,e][1,4]diazepin-11-one;

(g) cis-5,10-dihydro-5-{[(1,2-dimethyl-4-piperidinyl)amino]carbonyl}-11H-dibenzo[b,e][1,4]diazepin-11-one;

(h) trans-5,10-dihydro-5-{[(1,2-dimethyl-4-piperidinyl)-amino]carbonyl}-11H-dibenzo[b,e][1,4]diazepin-11-one;

(i) cis-5,10-dihydro-5-{[(1,3-dimethyl-4-piperidinyl)amino]carbonyl}-11H-dibenzo[b,e][1,4]diazepin-11-one;

(j) trans-5,10-dihydro-5-{[(1,3-dimethyl-4-piperidinyl)-amino]carbonyl}-11H-dibenzo[b,e][1,4]diazepin-11-one;

(k) 5,10-dihydro-5-{[(4-methyl-1-piperazinyl)amino]-carbonyl}-11H-dibenzo[b,e][1,4]diazepin-11-one;

(l) 5,10-dihydro-5-{[(3,4-dimetnyl-1-piperazinyl)amino]carbonyl}-11H-dibenzo[b,e][1,4]diazepin-11-one;

(m) 5,10-dihydro-5-{[(2,4-dimethyl-1-piperazinyl)amino]carbonyl}-11H-dibenzo[b,e][1,4]diazepin-11-one;

(n) 5,10-dihydro-5-{[(4-methyl-1-piperazinyl)oxy]carbonyl}-11H-dibenzo[b,e][1,4]diazepin-11-one;

(o) 5,10-dihydro-5-{[(3,4-dimethyl-1-piperazinyl)oxy]-carbonyl}-11H-dibenzo[b,e][1,4]diazepin-11-one;

(p) 5,10-dihydro-5-{[(2,4-dimethyl-1-piperazinyl)oxy]-carbonyl}-11H-dibenzo[b,e][1,4]diazepin-11-one;

(q) endo-5,10-dihydro-5-{[(8-methyl-8-azabicyclo[3.2.-1]oct-3-yl)oxy]carbonyl}-11H-dibenzo[b,e][1,4]diazepin-11-one;

(r) exo-5,10-dihydro-5-{[(8-methyl-8-arabicyclo[3.2.-1]oct-3-yl)oxy]carbonyl}-11H-dibenzo[b,e][1,4]diazepin-11-one;

(s) endo-5,10-dihydro-5-{[(8-methyl-8-azabicyclo[3.2.-1]oct-3-yl)oxy]carbonyl}-11H-dibenzo b,e][1,4]diazepin-11-one;

(t) exo-5,10-dihydro-5-{[(8-methyl-8-azabicyclo[3.2.-1]oct-3-yl)amino]carbonyl}-11H-dibenzo[b,e][1,4-]diazepin-11-one;

(u) 5,10-dihydro-5-{[N-methyl-N-(1-methyl-4-piperidinyl)amino]carbonyl}-11H-dibenzo[b,e][1,4-]diazepin-11-one;

(v) cis-5,10-dihydro-5-{[N-methyl-N-(1,2-dimethyl-4-piperidinyl)amino]carbonyl}-11H-dibenzo[b,e][1,4-]diazepin-11-one;

(w) trans-5,10-dihydro-5-{[N-methyl-N-(1,2-dimethyl-4-piperidinyl)amino]carbonyl}-11H-dibenzo[b,e][1,4-]diazepin-11-one;

(x) cis-5,10-dihydro-5-{[N-methyl-N-(1,3-dimethyl-4-piperidinyl)amino]carbonyl}-11H-dibenzo[b,e][1,4-]diazepin-11-one;

(y) trans-5,10-dihydro-5-{[N-methyl-N-(1,3-dimethyl-4-piperidinyl)amino]carbonyl}-11H-dibenzo[b,e][1,4-]dibenzo[b,e][1,4]diazepin-11-one; and (z) 5,10-dihydro-5-{[N-methyl-(4-methyl-1-piperazinyl)amino]-carbonyl}-11H-dibenzo[b,e][1,4]diazepin-11-one.

The substituted dibenzodiazepinones of Formula I and the acid addition salts thereof have valuable properties which make them commercially viable, and they are characterized in particular by an excellent protective effect on the stomach and intestines in warm-blooded animals. For example, they inhibit the formation of gastric ulcers. Moreover, they have a useful therapeutic range, due to their low toxicity and the absence of any significant side effects.

The excellent activity of the pharmacologically active compounds of Formula I and of their pharmacologically acceptable, i.e., biologically acceptable, acid addition salts makes it possible to use them in both human and veterinary medicine, for the treatment and prophylaxis of diseases based upon disorders of the stomach or intestins. They may be used, for example, to treat acute and chronic gastric and duodenal ulcers, gastritis, and gastric hyperacidity in humans and animals.

For such treatment, the compounds of Formula I and their pharmacologically acceptable salts can be incorporated, optionally in combination with other active ingredients, in manner known per se, into the usual pharmaceutical preparations such as tablets, coated tablets, capsules, powders, infusions, suppositories, solutions, or suspensions. The daily dose for adults is from about 0.75 to 375 mg (from about 0.01 to 5 mg/kg), preferably from about 3.75 to 188 mg (from about 0.05 to 2.5 mg/kg), more particularly, from about 7.5 to 112.5 mg (from about 0.1 to 1.5 mg/kg), generally administered in the form of several, preferably from 1 to 3, individual doses to achieve the desired results. Dependent upon the type and body weight of the patient to be treated, on the type and severity of the disease, on the type of preparation and on the route of administration as well as on the period or interval over which the administration takes place, it may, however, be necessary to deviate from the above dosages. Thus, it may be sufficient in some cases to administer more or less than the above-mentioned amounts of active ingredient. The optimum dosage and route of administration of the active ingredients which are necessary in each case can easily be determined by one skilled in the art.

The invention further relates to pharmaceutical compositions containing the compounds of Formula I. Similarly, the invention relates to the use of the compounds according to the invention in the preparation of pharmaceutical compositions used in the treatment of the diseases mentioned above.

If the substituted dibenzodiazepinones of Formula I and/or the pharmacologically acceptable acid addition salts thereof are to be used to treat the diseases mentioned above, the pharmaceutical preparations may also contain one or more pharmacologically active components, i.e., active ingredients, from other groups of medicaments. Examples of such other active ingredients include antacids, such as, aluminium hydroxide or magnesium aluminate; secretion-inhibitors such as H₂ blockers, for instance, cimetidine or ranitidine; gastric and intestinal therapeutic agents such as metoclopramide, bromoprid, or tiaprid; tranquilizers such as benzodiazepines, for instance, diazepam or oxazepam; spasmolytics such as bietamiverine or camylofine; anticholinergics such as oxyphencyclimine or phencarbamide; glucocorticoids such as prednisolone, fluocortolone, or betamethasone; non-steroidal antiphlogistic agents such as arylacetic acids, arylpropionic acids, heteroarylacetic acids, heteroarylpropionic acids, benzothiazine carboxamide dioxides, pyrazolidinediones, or quinazolinones, for instance, ibuprofen, naproxen, diclofenac, fenbufen, flurbiprofen, indomethacin, lonazolac, sudoxicam, piroxicam, phenylbutazone, bumadizon-calcium, or proquazone; and local anaesthetics such as tetracaine or procaine. Optionally, enzymes, vitamins, amino acids, or the like, may also be present.

Another aspect of the invention relates to processes for the preparation of substituted dibenzodiazepinones of Formula I as well as the acid addition salts thereof. These compounds can be prepared as follows:

METHOD A

Compounds of Formula I can be prepared by reacting compounds of the formula

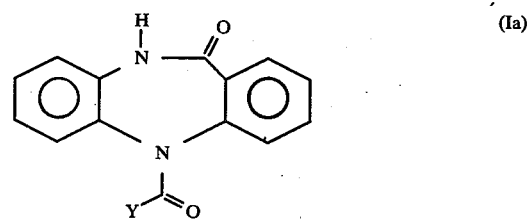

wherein Y is halogen, preferably bromine or chlorine, or the group $OR_1$, where $R_1$ is alkyl having from 1 to 5 carbon atoms, optionally substituted by one or more halogens, phenyl optionally substituted by one or more halogen or nitro groups, or aralkyl having from 7 to 15 carbon atoms, with compounds of the formula

wherein X and R are as defined above. The $R_1$ group may, for example, be methyl, ethyl, n-butyl, isobutyl, benzyl, 9-fluorenylmethyl, phenyl, 4-nitrophenyl, 2,2,2-trichloroethyl, 2,4,5-trichlorophenyl, or 2,2,2-trichloro-tert.butyl.

The reaction may be carried out without solvent or, preferably, in the presence of inert solvent, e.g., water, toluene or an alcohol such as methanol, ethanol, or isopropanol, but more preferably in the presence of an aprotic polar solvent such as, e.g., tetrahydrofuran, 1,4-dioxane, acetonitrile, N,N-dimethylformamide, dimethylsulfoxide, hexamethylphosphoric acid triamide, or a mixture thereof. The reaction is carried out at temperatures between 0° C. and the boiling point of the reaction mixture, preferably at from about 40° to 100° C. It has proven helpful to use additional inorganic or organic bases, e.g., alkali metal or alkaline earth metal hydroxides, alkoxides, or carbonates such as sodium hydroxide, sodium methoxide, potassium tert.butoxide, sodium carbonate, or potassium carbonate or tertiary amines such as triethylamine, ethyl diisopropylamine, N,N-dimethylaniline, or pyridine, and to perform the reaction in the presence of an excess of a compound of Formula II.

Good results can also be obtained by reaction of a dibenzodiazepinone of Formula Ia with a metal compound of the formula $$M-X-R \quad \text{(IIa)}$$

wherein X and R are as defined above and M represents an alkali metal atom or one equivalent of an alkaline earth metal atom. Metal compounds of Formula IIa can be readily prepared in situ from compounds of Formula II by reaction with alkali metals or alkaline earth metals, e.g., sodium, potassium, or barium, or with alkali metal or alkaline earth metal hydrides, e.g., sodium, potassium, or calcium hydride, or by reaction with alkali or alkaline earth organometallic compounds, e.g., n-butyllithium or phenyllithium.

METHOD B

The compounds of Formula I may also be prepared by reaction of 5,10-dihydro-11H-dibenzo[b,e][1,4]diazepin-11-one with chlorocarbonic acid derivatives of the formula

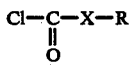

$$\text{(IV)}$$

or with isocyanates of the formula $$O=C=N-R \quad \text{(IVa)}$$

wherein X and R are as defined above. The reaction is carried out in inert organic solvents, for example, in aromatic hydrocarbons such as toluene or xylene; in ethers such as diisopropylether, tetrahydrofuran, or dioxane; in ketones such as pentan-3-one; in chlorinated aliphatic hydrocarbons such as 1,2-dichloroethane; or in other solvents such as acetonitrile or dimethylformamide, or in mixtures thereof, optionally in the presence of tertiary organic bases such as pyridine. Moreover, the reaction is carried out at temperatures up to the boiling point of the reaction mixture, preferably at temperatures of from about 30° to 100° C.

METHOD C

A further preparation procedure comprises reaction of 5,10-dihydro-11H-dibenzo[b,e][1,4]diazepin-11-one with a lithium-alkyl or lithium-aryl to from the di-lithium salt thereof and subsequent reaction of the di-lithium salt with a compound of the formula

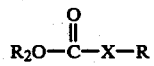

$$\text{(V)}$$

wherein X and R are as defined above and $R_2$ is alkyl having from 1 to 10 carbon atoms, preferably 1 to 6 carbon atoms, or aralkyl having from 7 to 13 carbon atoms, preferably phenylmethyl, phenylethyl, or phenylpropyl. X preferably represents an oxygen atom.

The conversion of the 5,10-dihydro-11H-dihydro[b,e][1,4]diazepin-11-one into the di-lithium salt thereof may be carried out with lithium alkyls but is more particularly carried out with n-butyllithium, n-butyllithium in the presence of tetramethyl ethylenediamine, tert.butyllithium, lithium diisopropylamide, lithium dicyclohexylamide, or lithium aryls such as lithium phenyl. Conversion into the lithium salt and further reaction with a compound of Formula V are carried out in an organic solvent at temperatures of from about −60° C. to 0° C., but preferably at about −10° C. The organic solvents used are those which are conventionally used for reactions with lithium alkyls or lithium aryls, for example, tetrahydrofuran, ethers such as diethyl ether, aliphatic hydrocarbons such as hexane, or mixtures of these solvents. Optionally a co-solvent such as hexamethyl phosphoramide may also be added. Shortly after the addition of lithium alkyl or lithium aryl is complete, a stoichiometric quantity or a slight excess of the ester of Formula V is added, and the reaction mixture is allowed to return slowly to ambient temperature, within, for example, two hours, to complete the reaction. The compound of Formula I, isolated according to conventional methods, can subsequently be converted into the salts thereof.

Bases of Formula I thus obtained can subsequently be converted into the acid addition salts thereof, or any acid addition salts obtained may be converted into the free bases or other pharmacologically acceptable acid addition salts.

Some of the dibenzodiazepinones of Formula I according to the invention contain one or two asymmetric carbon atoms in the —CO—X—R side chain. These compounds may therefore occur in two diastereomeric cis and trans forms or as the enantiomeric (+) and (−) forms. The invention includes the individual isomers and the mixtures thereof.

The diastereomers may be separated on the basis of their different physico-chemical properties, e.g., by fractional recrystallization from suitable solvents, by high pressure liquid chromatography, or by gas chromatography. Only one diastereomer is obtained if the methods of synthesis described above are carried out with only one diastereomer of Formula II or IIa.

Any racemates of the compounds of Formula I may be separated according to known methods, for example, by use of an optically active acid such as (+)- or (−)-tartaric acid or a derivative thereof, such as (+)- or (−)-diacetyl tartaric acid, (+)- or (−)-monomethyl tartrate, or (+)-camphorsulfonic acid.

In a conventional method for separating isomers, the racemate of a compound of Formula I is reacted with an equimolar quantity of one of the above-mentioned optically active acids in a solvent, and the crystalline optically active salts obtained are separated on the basis of their different solubilities. This reaction may be carried out in any type of solvent provided that the salts have sufficiently different solubilities therein. Preferably, methanol, ethanol, or a mixture thereof, for example, in proportions of 50:50 by volume, is used. Then, each of the optically active salts is dissolved in water and neutralized with a base such as sodium carbonate or potassium carbonate, and in this way the corresponding free compound is obtained in the (+) or (−) form.

Only one enantiomer is obtained if the methods of synthesis described above are carried out with only one enantiomer of Formula II or IIa.

The starting compounds of Formula Ia can be prepared by reaction of 5,10-dihydro-11H-dibenzo[b,e][1,4]diazepin-11-one, which is known from the literature, with halocarbonic acid derivatives of the formula

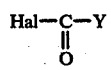

$$\text{(III)}$$

wherein Hal represents bromine or, preferably, chlorine and Y is as defined above. The reaction is carried out in inert organic solvents, examples of which include aromatic hydrocarbons, such as toluene, chlorobenzene, or xylene; open-chained or cyclic ethers such as diisopropylether, tetrahydrofuran, or dioxane; open-chained or cyclic aliphatic ketones such as pentan-3-one; and chlorinated aliphatic hydrocarbons such as 1,2-dichloroethane, or in other solvents such as acetonitrile, dimethylformamide, or a mixture thereof, and preferably in the presence of a tertiary organic base, preferably pyridine. Moreover, the reaction is carried out at temperatures up to, at most, the boiling point of the solvent or mixture of solvents used, preferably from about 30° to 80° C.

In this way, the following compound was obtained, for example: 5-chlorocarbonyl-5,10-dihydro-11H-dibenzo[b,e][1,4]diazepin-11-one, m.p.: 267°–268° C. (D).

The starting compounds of Formula II are known or may be prepared by procedures analogous to processes known from the literature. For example, 1-hydroxy-4-methylpiperazine is obtained as described by S. M. Riba, A. S. Issa, and Y. A. Beltagy, Pharmazie 33, 711 (1978), by reacting bis-[N-(2-chloroethyl)]-methylamine with hydroxylamine hydrochloride in an aqueous ethanolic solution and in the presence of potassium carbonate; 3α-aminotropane and 3α-methylaminotropane are obtained according to S. Archer et al., J. Amer. Chem. Soc. 79, 4194–4198 (1957); 3β-aminotropane is obtained according to R. Willstätter et al., Ber. dtsch. chem. Ges. 31, 1202 (1898); and pseudotropine is obtained as described by J. J. Tufariello et al., J. Amer. Chem. Soc. 101, 2435–2442 (1979).

Halocarbonic acid derivatives of Formula III are known.

Chlorocarbonic acid derivatives of Formula IV and isocyanates of Formula IVa are known or can be obtained using methods known from the literature [cf., for example, I.W. Mathison et al., J. Pharm. Sci. 62, 158 (1963); H. Hopff and H. Ohlinger, Angew, Chem. 61 183 (1949); W. Sieften, Liebigs Ann. Chem. 562, 75 (1949); Houben-Weyl VIII, 117; Ullmann V, 72; L. C. Raiford and K. Alexander, J. Org. Chem. 5, 306 (1940); H. H. Saunders and R. J. Slocombe, Chem. Rev. 43, 203 (1948); R. J. Slocombe, E. E. Hardy, J. H. Saunders, and R. L. Jenkins, J. Amer. Chem. Soc. 72, 1888 (1950); and H. Habad and A. G. Zeiler, Chem. Rev. 73, 75 (1975)].

The esters of Formula V are known from the literature or may be prepared using methods known from the literature.

As already mentioned above, the novel compounds of Formula I have valuable pharmacological properties. In particular, they have anti-ulcerogenic effects, they inhibit gastric acid secreation, and they have favorable effects on various other disorders of the gastrointestinal tract, including, in particular, irritable colon.

A favorable relation between anti-ulcerogenic and anti-secretory effects, on the one hand, and the undesirable effects on pupil size and the secretion of tears and saliva, on the other hand, which occurs particularly with therapeutic agents having an anti-cholinergic component, is of particular importance in the therapeutic use of the substances. The following tests show that the compounds according to the invention have surprisingly favorable characteristics in this respect.

1. INVESTIGATION OF THE SELECTIVITY OF THE ANTIMUSCARINIC ACTIVITY

Objects

Oxotremorine, a specific against for muscarinic receptors produces lesions in the mucous membrane of the stomach in rats and increases their secretion of saliva. This test method was chosen so that any selective activity of an antimuscarinic substance on the stomach could be identified.

Method

Ten female albino rats (of the Crl:COBS-CD (SD) BR strain) with a body weight of from 120 to 150 gm apiece were used in each treatment group and were kept without food for 24 hours before the start of the test but given free access to drinking water.

To determine, in preliminary tests, the muscarinic effect of oxotremorine on each of the symptons studies, a dosage/activity curve was drawn up with at least three dosages for each symptom.

When the antimuscarinic substances were tested, the dosage of oxotremorine which triggered the symptom in question in 90 to 100% of the animals in the preliminary tests was used.

Lesions in the mucous membrane of stomach: 0.62 mg/kg i.v.

Secretion of saliva: 0.083 mg/kg i.v.

Each antimuscarinic substance was administered intravenously in uniformly graduated doses 15 minutes before the oxotremorine was administered. Control groups were given corresponding quantities of the solvent and suspension agent instead of the test substance. Immediately after the oxotremorine was administered, the animals were placed in a glass case for 15 minutes and observed.

The test for the effect on the oxotremorine-induced secretion of saliva was carried out as a blind test, i.e., the tester did not know which treatment the animals had been given.

The results were expressed as the percentage inhibition of the oxotremorine effect (the percentage of animals which did not show the symptom in question). The $ED_{50}$ values were determined using the method described by LITCHFIELD and WILCOXON (J. Pharmacol. Exp. Ther. 96, 99, 1949).

The effects on lesions of the nucous membrane of the stomach were evaluated as follows:

The lesions of the gastric mucous membrane were produced by intravenous injection of 0.62 mg/kg of oxotremorine 30 minutes after the oral administration of 1 mg/kg of neostigmine (a cholinesterase inhibitor). Sixty minutes after the administration of the neostigmine, the animals were killed, and the stomachs were removed, opened, and examined for the presence of any lesions in the mucous membrane. The protective effect of the test substances was expressed as the percentage inhibition (percentage of animals with lesions).

The $ED_{50}$ and $ED_{70}$ values were determined using the method of LITCHFIELD and WILCOXON (eee above).

2. TESTING FOR MYDRIASIS

The effect of the test substances on the pupil size in rats was investigated as follows:

The substances were administered intravenously to groups of 10 animals in at least three uniformly graduated doses. The pupil size was then observed for 10 minutes to see if there were any changes (mydriasis or miosis. Again, the test was carried out blind, i.e., the tester did not know what preliminary treatment the animals had received. The percentage of test animals in which mydriasis occurred was determined. The $ED_{50}$ values were again determined using the method of LITCHFIELD and WILCOXON (see above).

3. STUDIES OF BINDING TO MUSCARINIC RECEPTORS: DETERMINATION OF THE $IC_{50}$ VALUES

The organ donors were male Sprague-Dawley rats with a body weight of from about 180 to 220 gm each. After the heart, stomach, and cerebral cortex had been removed, the remainder of the operation was carried out in ice-cold Hepes-HCl buffer (pH 7.4; 100 m molar NaCl, 10 m molar $MgCl_2$). The smooth muscle of the fundus of the stomach was separated from the mucous membrane of the stomach and subjected to preliminary homogenization. The whole heart was cut up with scissors. All the organs were then homogenized in a Potter apparatus.

For the binding test, the homogenized organs were diluted as follows:
Smooth muscle of the fundus of the stomach: 1:100
Whole heart: 1:250
Cerebral cortex: 1:3000

The homogenized organ preparations were incubated at a specific concentration of the radioligand and with a series of concentrations of the non-radioactive test substances in an Eppendorf centrifuge tube at 30° C. The duration of incubation was 45 minutes. As substance 0.3 n molar $^3$H-N-methylscopolamine ($^3$H-NMS) was used as the radioligand. After incubation had been brought to an end by centrifuging at 14000 g, the radioactivity in the pellet was determined. It represents the sum of the specific and non-specific binding of $^3$H-NMS. The proportion of non-specific binding was defined as the radioactivity which was bound in the presence of $1\mu$ molar quinuclidinylbenzylate. Four measurements were taken in each case. The $IC_{50}$ values of the non-labelled test substances were determined graphically. They represent the concentration of test substance at which the specific binding of $^3$H-NMS to the muscarinic receptors in the various organs was inhibited by 50%.

The following compounds, examples of compounds of Formula I, were tested as described above:
A=5,10-dihydro-5-{[(1-methyl-4-piperidinyl)oxy]carbonyl}-11H-dibenzo[b,e][1,4]diazepin-11-one;
B=5,10-dihydro-5-{[(1-methyl-4-piperidinyl)amino]carbonyl}-11H-dibenzo[b,e][1,4]diazepin-11-one; and
C=5,10-dihydro-5-{[(4-methyl-1-piperazinyl)amino]carbonyl}-11H-dibenzo[b,e][1,4]diazepin-11-one.
The testing results are set forth in the following table:

the novel compounds of Formula I differentiate between muscarinic receptors in different types of tissue. This is clear from the considerably lower $IC_{50}$ values in the tests on preparations from the cerebral cortex compared with those of the smooth muscle of the stomach and the heart.

The pharmacological data in the above table show—in complete agreement with the receptor binding studies—that the formation of oxotremorine-induced lesions in the mucous membrane of the stomach is inhibited by the above-mentioned compounds even at doses at which no restriction of salivation and no mydriasis can be observed.

The following examples are intended to illustrate the invention and should not be construed as limiting the invention thereto. In the examples, "M.p." or "m.p." indicates "melting point" and "D" indicates "decomposition".

EXAMPLE 1

5,10-Dihydro-5-{[(1-methyl-4-piperidinyl)amino]carbonyl}-11H-dibenzo[b,e][1,4]diazepin-11-one Amounts of 3.2 gm (0.012 mol) of 5-chlorocarbonyl-5,10-dihydro-11H-dibenzo[b,e][1,4]diazepin-11-one and 2.1 gm (0.02 mol) of sodium carbonate were refluxed in 100 ml of acetonitrile together with 2.3 ml (0.02 mol) of 4-amino-1-methyl-piperidine for 15 minutes under stirring. The mixture was filtered while hot, and the filtrate was purified over a silica gel column [eluant: acetonitrile; followed by methylene chloride/ethyl acetate/cyclohexane/methanol/ammonia (175:75:23:23:3)]. The desired fraction was concentrated by evaporation in vacuo, and the residue was recrystallized from 50% aqueous acetonitrile.

M.p.: 128°–130° C. Yield: 56% of theory.

By use of analogous procedures, the following compounds were prepared:
(a)  cis-5,10-dihydro-5-{[(1,2-dimethyl-4-piperidinyl)amino]carbonyl}-11H-dibenzo[b,e][1,4]diazepin-11-one;
(b)  trans-5,10-dihydro-5-{[(1,2-dimethyl-4-piperidinyl)amino]carbonyl}-11H-dibenzo[b,e][1,4]diazepin-11-one;
(c)  cis-5,10-dihydro-5-{[(1,3-dimethyl-4-piperidinyl)amino]carbonyl}-11H-dibenzo[b,e][1,4]diazepin-11-one;
(d)  trans-5,10-dihydro-5-{[(1,3-dimethyl-4-piperidinyl)amino]carbonyl}-11H-dibenzo[b,e][1,4]diazepin-11-one:
(e)  exo-5,10-dihydro-5-{[(8-methyl-8-azabicyclo[3.2.1]oct-3-yl) amino]carbonyl}-11H-dibenzo[b,e][1,4]diazepin-11-one, m.p.: 209°–211° C. (pentan-3-one).

TABLE

| Substance | Receptor binding tests $IC_{50}$ [n mol $l^{-1}$] | | | Oxotremorine Test [µg/kg] i.v. | | | Mydriasis $ED_{50}$ i.v. [µg/kg] |
| | | | | Anti-ulcerative Effect | | Inhibition of Salivation | |
| | Cortex | Smooth Muscle Fundus of Stomach | Heart | $ED_{50}$ | $ED_{70}$ | $ED_{50}$ | |
| --- | --- | --- | --- | --- | --- | --- | --- |
| A | 5.5 | 60 | 42 | 15.5 | 36 | 64 | 71 |
| B | 13 | 100 | 75 | 2.5 | 4.8 | 22 | 23 |
| C | 18 | 90 | — | 3.6 | 7 | 32 | 82.5 |

The results in the above table show that the compounds mentioned generally have a high affinity with muscarinic receptors. Moreover, the results show that

EXAMPLE 2

5,10-Dihydro-5-{[N-methyl-N-(1-methyl-4-piperidinyl)amino]carbonyl}-11H-dibenzo[b,e][1,4]diazepin-11-one Nine grams (0.033 mol) of 5-chlorocarbonyl-5,10-dihydro-11H-dibenzo[b,e][1,4]diazepin-11-one, 5.3 gm (0.05 mol) of sodium carbonate, and 5.2 gm (0.036 mol) of 1-methyl-4-methylamino-piperidine were refluxed in 150 ml of acetonitrile for 15 minutes under stirring. The mixture was filtered while hot, and then the filtrate was placed on a silica gel column and eluted first with acetonitrile and then with a methylene chloride/ethyl acetate/cyclohexane/methanol/ammonia (175:75:23:23:3) mixture. The desired fraction was concentrated by evaporation in vacuo, and the residue was recrystallized from acetonitrile.

M.p.: 232°–234° C. Yield: 62% of theory.

By use of analogous procedures, the following compounds were prepared:
(a) cis-5,10-dihydro-5-{[N-methyl-N-(1,2-dimethyl-4-piperidinyl) amino]carbonyl}-11H-dibenzo[b,e][1,4]-diazepin-11-one;
(b) trans-5,10-dihydro-5-{[N-methyl-N-(1,2-dimethyl-4-piperidinyl) amino]carbonyl}-11H-dibenzo[b,e][1,4]-diazepin-11-one;
(c) cis-5,10-dihydro-5-{[N-methyl-N-(1,3-dimethyl-4-piperidinyl) amino]carbonyl}-11H-dibenzo[b,e][1,4]-diazepin-11-one;
(d) trans-5,10-dihydro-5-{[N-methyl-N-(1,3-dimethyl-4-piperidinyl) amino]carbonyl}-11H-dibenzo[b,e][1,4]-diazepin-11-one;
(e) endo-5,10-dihydro-5-{[N-methyl-N-(8-methyl-8-azabicyclo[3.2.1]oct-3-yl)amino]carbonyl}-11H-dibenzo[b,e][1,4]-diazepin-11-one, m.p.: 242°–245° C. (acetonitrile);
(f) exo-5,10-dihydro-5-{[N-methyl-N-(8-methyl-8-azabicyclo[3.2.1]oct-3-yl)amino]carbonyl}-11H-dibenzo[b,e][1,4]-diazepin-11-one; and
(g) 5,10-dihydro-5-{[N-methyl-(4-methyl-1-piperazinyl)amino]carbonyl}-11H-dibenzo[b,e][1,4]diazepin-11-one,
m.p.: 297° C. [methanol/ethyl acetate (1:2)].

EXAMPLE 3

5,10-Dihydro-5-{[(4-methyl-1-piperazinyl)amino]carbonyl}-11H-dibenzo[b,e][1,4]diazepin-11-one A mixture of 5.5 gm (0.0202 mol) of 5-chlorocarbonyl-5,10-dihydro-11H-dibenzo[b,e][1,4]diazepin-11-one, 8.6 gm (0.075 mol) of 1-amino-4-methylpiperazine, and 200 ml of anhydrous dioxane was heated for 30 minutes over a steam bath. Then, 2 gm of active charcoal were added to the resulting cloudy reaction mixture while it was still hot, the mixture was filtered, and the filtrate obtained was concentrated by evaporation in vacuo. The residue was purified by column chromatography on 300 gm of silica gel [eluant: dichloromethane/methanol/conc. aqueous ammonia mixture (volume ratio of 800:200:5)]. The residue remaining after the eluates had been concentrated was taken up in 500 ml of ethyl acetate, 1 gm of active charcoal was added, and the resulting mixture was boiled, filtered, and concentrated by evaporation. Then, 300 ml of methanol were added, and the resulting mixture was filtered while hot and evaporated to dryness. After recrystallization from ethanol, 1.8 gm (25% of theory) of colorless crystals were obtained, m.p.: 213°–214° C. (D).

By use of analogous procedures, the following compounds were prepared:
(a) 5,10-dihydro-5-{[(3,4-dimethyl-1-piperazinyl)amino]carbonyl}-11H-dibenzo[b,e][1,4]diazepin-11-one;
(b) 5,10-dihydro-5-{[(2,4-dimethyl-1-piperazinyl)amino]carbonyl}-11H-dibenzo[b,e][1,4]diazepin-11-one;
(c) endo-5,10-dihydro-5-{[N-methyl-N-(8-methyl-8-azabicyclo[3.2.1]oct-3-yl)amino]carbonyl}-11H-dibenzo[b,e][1,4]diazepin-11-one, m.p.: 242°–245° C. (acetonitrile); and
(d) 5,10-dihydro-5-{[N-methyl-N-(1-methyl-4-piperidinyl)amino]carbonyl}-11H-dibenzo[b,e][1,4]diazepin-11-one, m.p.: 232°–233° C. (acetonitrile).

EXAMPLE 4

5,10-Dihydro-5-{[(1-methyl-4-piperidinyl)oxy]carbonyl}-11H-dibenzo[b,e][1,4]diazepin-11-one A quantity of 4.1 gm (0.015 mol) of 5-chlorocarbonyl-5,10-dihydro-11H-dibenzo[b,e][1,4]diazepin-11-one was refluxed with 3.45 gm (0.03 mol) of 1-methyl-4-piperidinol in 50 ml of chlorobenzene for two hours. After cooling, the reaction solution was diluted by the addition of 200 ml of ethyl acetate and then extracted exhaustively with 15% hydrochloric acid. The combined extracts were neutralized with potassium carbonate and extracted several times with chloroform, and the combined chloroform extracts were evaporated to dryness in vacuo. By recrystallization from ethyl acetate, colorless crystals were obtained, m.p.: 203°–204° C. Yield: 1.2 gm (23% of theory).

By use of analogous procedures, the following compounds were prepared:
(a) cis-5,10-dihydro-5-{[(1,2-dimethyl-4-piperidinyl)oxy]carbonyl}-11H-dibenzo[b,e][1,4]diazepin-11-one
(b) trans-5,10-dihydro-5-{[(1,2-dimethyl-4-piperidinyl)oxy]carbonyl}-11H-dibenzo[b,e][1,4]diazepin-11-one;
(c) cis-5,10-dihydro-5-{[(1,3-dimethyl-4-piperidinyl)oxy]carbonyl}-11H-dibenzo[b,e][1,4]diazepin-11-one;
(d) trans-5,10-dihydro-5-{[(1,3-dimethyl-4-piperidinyl)oxy]carbonyl}-11H-dibenzo[b,e][1,4]diazepin-11-one;
(e) 5,10-dihydro-5-{[(4-methyl-1-piperazinyl)oxy]carbonyl}-11H-dibenzo[b,e][1,4]diazepin-11-one;
(f) 5,10-dihydro-5-{[(3,4-dimethyl-1-piperazinyl)oxy]carbonyl}-11H-dibenzo[b,e][1,4]diazepin-11-one;
(g) 5,10-dihydro-5-{[(2,4-dimethyl-1-piperazinyl)oxy]carbonyl}-11H-dibenzo[b,e][1,4]diazepin-11-one;
(h) endo-5,10-dihydro-5-{[(8-methyl-8-azabicyclo[3.2.1]oct-3-yl) oxy]carbonyl}-11H-dibenzo[b,e][1,4]diazepin-11-one,
$R_f$ value: 0.55 [eluant: methylene chloride/cyclohexane/methanol/ammonia (68:15:15:2), ready-made silica gel plate 60 $F_{254}$];
(i) exo-5,10-dihydro-5-{[(8-methyl-8-azabicyclo[3.2.1]oct-3-yl) oxy]carbonyl}-11H-dibenzo[b,e][1,4]diazepin-11-one; and
(j) 5,10-dihydro-5-{[(4-methyl-4-piperidinyl)oxy]carbonyl}-11H-dibenzo[b,e][1,4]diazepin-11-one, m.p. 178°–179° C. (diethylether).

EXAMPLE 5

5,10-Dihydro-5-{[(1-methyl-4-piperidinyl)oxy]carbonyl}-11H-dibenzo[b,e][1,4]diazepin-11-one A quantity of 4.9 gm (0.0425 mol) of 1-methyl-4-piperidinol was added dropwise to a mixture of 22.5 ml of a 20% solution of phosgene in toluene, 100 ml of dioxane, and 4.75 gm (0.045 mol) of anhydrous sodium carbonate while external cooling with ice was carried out. The mixture was stirred for a further 60 minutes at ambient temperature, 9.0 gm (0.0428 mol) of 5,10-dihydro-11H-dibenzo[b,e][1,4]diazepin-11-one were added to the reaction mixture, and this was then refluxed for four hours. The mixture was filtered, the filtrate was concentrated by evaporation in vacuo, and the crude product obtained was purified by column chromatography on 500 gm of silica gel [eluant: ethyl acetate/methanol (volume ratio of 10:1)]. After recrystallization from ethyl acetate, the resulting colorless crystals melted at 203°-204° C. and were identical—according to the mixed melting point, thin layer chromatogram, and IR spectrum—to a product prepared according to Example 4. Yield: 7.6 gm (51% of theory).

By use of analogous procedures, the following compounds were prepared:
(a) 5,10-dihydro-5-{[(4-methyl-1-piperazinyl)oxy]carbonyl}-11H-dibenzo[b,e][1,4]diazepin-11-one; and
(b) endo-5,10-dihydro-5-{[(8-methyl-8-azabicyclo[3.2.1]oct-3-yl) oxy]carbonyl}-11H-dibenzo[b,e][1,4-]diazepin-11-one, $R_f$ value: 0.55 [ready-made silica gel plate 60 $F_{254}$; eluant: methylene chloride/cyclohexane/methanol/ammonia (68:15:15:2)].

EXAMPLE 6 endo-5,10-Dihydro-5-{[(8-methyl-8-azabicyclo[3.2.1]oct-3-yl)amino]carbonyl}-11H-dibenzo[b,e][1,4-]diazepin-11-one The above compound was prepared analogously to Example 1 from 5-chlorocarbonyl-5,10-dihydro-11H-dibenzo[b,e][1,4]diazepin-11-one and endo-3-amino-8-methyl-8-azabicyclo[3.2.1]octane, in a yield of 58% of theory.

Colorless crystals, m.p.: 264°-266° C. (acetonitrile).
$C_{22}H_{24}N_4O_2$ (376.46): Calculated: C 70.19; H 6.43; N 14.88. Found: C 79.90; H 6.53; N 14.94.

IR (CH$_2$Cl$_2$): NH 3450/cm, 3370/cm, CO 1660 and 1675/cm

UV (ethanol): Shoulder at λ235 (E=0.17) and λ272 nm (E=0.075)
(ethanol/KOH): Shoulder at λ250 nm (E=0.105); λmax 288 nm (E=0.075) (c=50 mg/l; layer thickness: 2 mm)

$^1$H-NMR (CDCl$_3$): δ=9.35 (1H-s; exchangeable H); 7.96 (1H-dd; J=5 and 2 Hz; ar.H); 7.0-7.7 (7H-m; ar.H); 4.94 (1H-d; J=5 Hz; exchangeable H); 3.7-4.1 (1H-m); 2.8-3.15 (2H-m); 2.21 (3H-s; N-CH$_3$); 1.0-2.2 ppm (8H-m).

EXAMPLE 7

5,10-Dihydro-5-{[(1-methyl-4-piperidinyl)oxy]carbonyl}-11H-dibenzo[b,e][1,4]diazepin-11-one Thirty-two milliliters (0.05 mol) of N-butyl-lithium (15% in n-hexane) were added dropwise, under stirring, to a solution of 5 gm (0.024 mol) of 5,10-dihydro-5H-dibenzo[b,e][1,4]diazepin-11-one in 150 ml of tetrahydrofuran, at 10° C. The mixture was stirred for a further 0.5 hours at ambient temperature, and then a solution of 5.6 gm (0.03 mol) of ethyl 1-methyl-piperidin-4-oxy-carboxylate in 25 ml of dry tetrahydrofuran was added dropwise—again at 10° C.—and the resulting mixture was stirred for two hours at ambient temperature. The reaction mixture was then evaporated down to about one-third of its volume in vacuo and mixed with ice-/water. The resulting mixture was extracted three times with ethyl acetate. The aqueous acidic portion was made alkaline with solid potassium carbonate, under cold conditions, and extracted three times more with ethyl acetate. These extracts were dried and concentrated by evaporation in vacuo. The residue, which was recrystallized from ethanol, yielded 3.4 gm (40% of theory) of 5,10-dihydro-5-{[(1-methyl-4-piperidinyl)oxy]carbonyl}-11H-dibenzo[b,e][1,4]diazepin-11-one, m.p.: 203°-204° C., which is identical in its physical properties to the product obtained according to Example 4.

The following examples are illustrative of a few pharmaceutical dosage unit compositions comprising a compound of the invention, namely, 5,10-dihydro-5-{[(1-methyl-4-piperidinyl) amino]carbonyl}-11H-dibenzo[b,e][1,4]diazepin-11-one, as active ingredient.

EXAMPLE 8

Tablets containing 5 mg of active ingredient

Each tablet is compounded from the following ingredients:

| Component | Amount (mg) |
|---|---|
| Active ingredient | 5.0 |
| Lactose | 148.0 |
| Potato starch | 65.0 |
| Magnesium stearate | 2.0 |
| TOTAL: | 220.0 |

Preparation

A 10% mucilage is prepared from potato starch by heating. The active ingredient, lactose, and remaining potato starch are mixed together and granulated with the mucilage through a screen with a mesh size of 1.5 mm. The granulate is dried at 45° C., passed through the screen again, mixed with magnesium stearate, and compressed to form tablets.
Weight of tablet: 220 mg
Punch: 9 mg

EXAMPLE 9

Coated tablets containing 5 mg of active ingredient

The tablets prepared according to Example 8 are coated by a known method with a shell consisting essentially of sugar and talc. The finished coated tablets are polished with beeswax.
Weight of coated tablet: 300 mg

EXAMPLE 10

Ampules containing 1 mg of active ingredient

Each ampule contains a solution having the following composition:

| Component | Amount |
|---|---|
| Active ingredient | 1.0 mg |
| Sodium chloride | 8.0 mg |

| Component | Amount |
|---|---|
| Distilled water q.s. ad | 1 ml |

Preparation

The active ingredient and sodium chloride are dissolved in distilled water and then topped up to the volume given. The solution is sterilized by filtration and transferred into 1 ml ampules.

Sterilization: 20 minutes at 120° C.

EXAMPLE 11

Suppositories containing 5 mg of active ingredient

Each suppository has the following composition:

| Component | Amount (mg) |
|---|---|
| Active ingredient | 5.0 |
| Suppository mass (e.g., WITEPSOL ® W 45, available from Chemische Werke Witten GmbH). | 1 695.0 |
| TOTAL: | 1 700.0 |

Preparation

The finely powdered active ingredient is suspended in the molten suppository mass, which has been cooled to 40° C. At 37° C. the mass is poured into slightly chilled suppository molds.

Weight of suppository: 1.7 gm

EXAMPLE 12

Drops containing 5 mg/ml of active ingredient

One hundred milliliters of drop solution have the following composition:

| Component | Amount |
|---|---|
| Active ingredient | 0.5 gm |
| Methyl p-hydroxybenzoate | 0.035 gm |
| Propyl p-hydroxybenzoate | 0.015 gm |
| Anise oil | 0.05 gm |
| Menthol | 0.06 gm |
| Pure ethanol | 10.0 gm |
| Sodium cyclamate | 1.0 gm |
| Glycerol | 15.0 gm |
| Distilled water q.s. ad | 100.0 ml |

Preparation

The active ingredient and sodium cyclamate are dissolved in about 70 ml of water, and glycerol is added thereto. The p-hydroxybenzoates, anise oil, and menthol are dissolved in the ethanol, and this solution is added to the aqueous solution, under stirring. Finally, the mixture is made up to 100 ml with water and filtered to remove any suspended particles.

Any one of the other compounds embraced by Formula I, or a combination thereof, may be substituted for the particular active ingredient employed in Examples 8 through 12. Likewise, the amount of active ingredient in these illustrative examples may be varied to achieve the dosage unit range set forth above, and the amounts and nature of the inert pharmaceutical carrier ingredient may be varied to meet particular requirements.

While the present invention has been illustrated with the aid of certain specific embodiments thereof, it will be readily apparent to others skilled in the art that the invention is not limited to these particular embodiments, and the various changes and modifications may be made without departing from the spirit of the invention or the scope of the appended claims.

We claim:

1. A compound of the formula

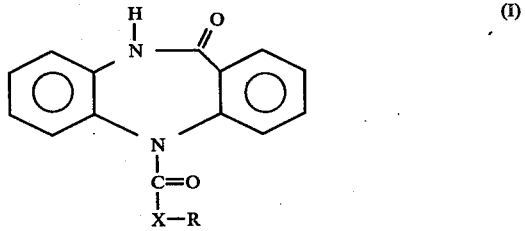

wherein
X is oxygen, —NH—, or —NCH$_3$— and
R is 1-methyl-4-piperidinyl, 4-methyl-1-piperazinyl, endo-8-methyl-8-azabicyclo[3.2.1]oct-3-yl, or exo-8-methyl-8-azabicyclo[3.2.1]oct-3-yl, each of which may optionally have an additional methyl substituent,
a diastereomer or enantiomer thereof, or a non-toxic, pharmacologically acceptable acid addition salt thereof with an inorganic or organic acid.

2. A compound of claim 1, wherein
X is oxygen or —NH— and
R is 1-methyl-4-piperidinyl or 4-methyl-1-piperazinyl, or a non-toxic, pharmacologically acceptable acid addition salt thereof with an inorganic or organic acid.

3. An anti-ulcerogenic pharmaceutical composition consisting essentially of an inert pharmaceutical carrier and an effective anti-ulcerogenic amount of a compound of claim 1.

4. The method of inhibiting the formation of gastric ulcers in a warm-blooded animal in need thereof, which comprises perorally, parenterally, or rectally administering to said animal an effective anti-ulcerogenic amount of a compound of claim 1.

* * * * *

UNITED STATES PATENT AND TRADEMARK OFFICE
CERTIFICATE OF CORRECTION

PATENT NO. : 4,443,452
DATED : April 17, 1984
INVENTOR(S) : WOLFHARD ENGEL et al.

It is certified that error appears in the above—identified patent and that said Letters Patent is hereby corrected as shown below:

Column 2, line 32, "dimetnyl" should read -- dimethyl --.

Column 2, line 51, the moiety "b,e]" should read -- [b,e] --.

Column 3, line 22, "intestins" should read -- intestines --.

Column 9, line 3, "miosis." should read -- miosis). --

Signed and Sealed this

Eighth Day of January 1985

[SEAL]

Attest:

Attesting Officer

GERALD J. MOSSINGHOFF
Commissioner of Patents and Trademarks